United States Patent
Davydov et al.

(10) Patent No.: US 10,307,233 B1
(45) Date of Patent: Jun. 4, 2019

(54) METHOD FOR UTILIZING A MANDIBULAR C-CLAMP TO IDENTIFY A FIXED POINT OF REFERENCE ON A HUMAN JAW

(71) Applicant: Albert Davydov, Forest Hills, NY (US)

(72) Inventors: Albert Davydov, Forest Hills, NY (US); Peter Usov, Belle Mead, NJ (US)

(73) Assignee: Albert Davydov, Forest Hills, NY (US)

( * ) Notice: Subject to any disclaimer, the term of this patent is extended or adjusted under 35 U.S.C. 154(b) by 0 days.

(21) Appl. No.: 15/865,600

(22) Filed: Jan. 9, 2018

(51) Int. Cl.
| | |
|---|---|
| *A61B 5/00* | (2006.01) |
| *A61C 19/04* | (2006.01) |
| *A61B 5/107* | (2006.01) |
| *A61C 11/00* | (2006.01) |
| *A61B 17/17* | (2006.01) |

(52) U.S. Cl.
CPC ............ *A61C 19/04* (2013.01); *A61B 5/1077* (2013.01); *A61C 11/00* (2013.01); *A61B 5/6802* (2013.01); *A61B 17/176* (2013.01)

(58) Field of Classification Search
CPC .... A61B 6/00; A61B 6/04; A61B 6/14; A61B 6/035; A61B 6/0407; A61B 6/4085; A61B 5/0077; A61B 5/6803; A61B 5/11; A61B 5/1038; A61B 5/00; A61B 6/145; A61C 19/05; A61C 19/045
USPC .................. 33/512–513; 433/44, 68; 606/54; 378/38–40, 168, 191; 382/131, 132
See application file for complete search history.

(56) References Cited

U.S. PATENT DOCUMENTS

| | | | | |
|---|---|---|---|---|
| 1,662,670 A | * | 3/1928 | Harter ..................... | A61B 5/107 33/514 |
| 1,823,184 A | * | 9/1931 | Beeler ..................... | A61C 19/04 33/513 |
| 1,944,601 A | * | 1/1934 | Gulick ..................... | A61C 19/04 33/513 |
| 1,976,045 A | * | 10/1934 | Sorenson ............... | A61C 19/00 33/513 |
| 2,107,534 A | * | 2/1938 | Houser ................... | A61B 5/107 33/513 |
| 2,315,660 A | * | 4/1943 | Sahr ...................... | A61C 9/0006 433/44 |
| 2,550,869 A | * | 5/1951 | Salisbury ............ | A61B 17/6433 433/44 |
| 2,701,915 A | * | 2/1955 | Page ..................... | A61C 11/022 433/69 |
| 2,832,137 A | * | 4/1958 | Moore .................. | A61C 19/045 433/73 |
| 4,843,720 A | * | 7/1989 | Kim ....................... | A61B 5/107 33/812 |

(Continued)

*Primary Examiner* — Wade Miles
*Assistant Examiner* — Matthew P Saunders
(74) *Attorney, Agent, or Firm* — Anna Vishev

(57) ABSTRACT

A method for precisely identifying a fixed point of reference on a human jaw including providing a mandibular c-clamp, which has a shaft, an upper prong fixedly connected to the shaft, a lower prong movable along the shaft, and a wedge configured to selectively secure the lower prong to the shaft. The upper prong of the mandibular c-clamp is inserted into a patient's mouth. The lower prong of the mandibular c-clamp is then moved along the shaft to close on a patient's chin compressing patient's soft tissue, and a position of the lower prong is secured on the shaft using the wedge so that the lower prong is no longer movable along the shaft. A sensor is then secured to a designated area of the mandibular c-clamp so as to provide a reference point.

3 Claims, 4 Drawing Sheets

(56) References Cited

U.S. PATENT DOCUMENTS

| | | | | |
|---|---|---|---|---|
| 4,907,251 | A | * | 3/1990 | Mork ........................ A61B 6/08 378/170 |
| 5,828,722 | A | * | 10/1998 | Ploetz ...................... A61B 6/08 378/38 |
| 5,971,756 | A | * | 10/1999 | Fjelstad ................. A61C 19/05 433/68 |
| 6,168,601 | B1 | * | 1/2001 | Martini ................ A61B 17/025 433/140 |
| 9,504,434 | B2 | * | 11/2016 | Bianconi .................. A61B 6/04 |
| D810,304 | S | * | 2/2018 | Mattiuzzo .................... D24/184 |
| 2003/0233761 | A1 | * | 12/2003 | Erskine-Smith ....... A61C 19/04 33/513 |
| 2006/0227939 | A1 | * | 10/2006 | Walker ..................... A61B 6/04 378/208 |
| 2006/0251220 | A1 | * | 11/2006 | Young ..................... A61C 1/084 378/204 |
| 2008/0253506 | A1 | * | 10/2008 | Zuendorf ................. A61B 6/14 378/18 |
| 2008/0299511 | A1 | * | 12/2008 | Thoms ..................... A61B 6/04 433/68 |
| 2015/0359493 | A1 | * | 12/2015 | Grant ....................... A61B 6/04 378/20 |
| 2017/0105686 | A1 | * | 4/2017 | Alric ..................... A61B 6/032 |

\* cited by examiner

10,307,233 B1

METHOD FOR UTILIZING A MANDIBULAR C-CLAMP TO IDENTIFY A FIXED POINT OF REFERENCE ON A HUMAN JAW

BACKGROUND OF THE INVENTION

This application and its disclosure generally relate to the field of positioning human jaws for dental procedures.

As described in U.S. Pat. No. 9,579,046, a position of a human head can be unambiguously determined using the described methods of 3D geometric modeling. Once such position is determined, however, it is desirable to secure the human head in such position or at least provide a fixed point of reference, which can then be used for subsequent dental and/or other procedures. In other words, it is desirable to provide a sensor reference point on the mandible, i.e., the lower jaw.

Cervicocranium is a complex anatomical structure consisting of C2, C1 and base of the Cranium. Present art of measuring mandibular movement involve fixing a magnet on the lower central teeth and picking up the tracings with a magnetic field frame within which the magnet is moving during opening and closing movements of the jaw. When mandible translates into full range of motion during opening and closing it may involve undetectable and unmeasurable cervicocranial movements, which can cause false positive and false negative mandibular ROM results if the measurement system does not provide for such compensation. Existing systems which are currently in the market lack a compensation element for the cervicocranial movements that makes their data erroneous.

Therefore, it is desirable to provide a sensor reference point compensating for the cervicocranial movements. Such sensor reference point should possess the following: it should be located outside of the mouth; it should be inexpensive and user-friendly in application; it should be simple and predictable in positioning, it should conform with all infection control requirements; it should not move once positioned and stay without movements while the mandibular tracings are taken; it should allow sufficient time for testing; it should be easily replaceable, if necessary; and it should be comfortable to all patient situations (with, or without regard to the presence of teeth)

Other methods and systems, currently in use, utilize dual inclinometers, bubble goniometers, radiographs, compass technology, visual estimation, ultrasound, geometric methods, digital optoelectronic instruments, computerized kinematic analysis using passive markers and infrared TV cameras, MRI or sensors attached to the subject's head for head orientation determination.

However, none of the existing systems is simple enough to use nor yields sufficient accuracy in identifying a particular reference point.

SUMMARY OF THE INVENTION

It is an object of the present invention to provide a method for precisely identifying a fixed point of reference on a human jaw that is accurate, reliable, user-friendly and portable with low-cost.

In its general aspect, the method includes providing a mandibular c-clamp, which includes a shaft, an upper prong fixedly connected to the shaft, a lower prong movable along the shaft, and a wedge configured to selectively secure the lower prong to the shaft. The upper prong of the dental c-clamp is inserted into a patient's mouth. The lower prong of the mandibular c-clamp is then moved along the shaft to close on a patient's chin compressing patient's soft tissue, and a position of the lower prong is secured on the shaft using the wedge so that the lower prong is no longer movable along the shaft. A sensor is then secured to a designated area of the mandibular c-clamp so as to provide a reference point.

The above aspects, advantages and features are of representative embodiments only. It should be understood that they are not to be considered limitations on the invention as defined by the claims. Additional features and advantages of the invention will become apparent in the following description, from the drawings, and from the claims.

BRIEF DESCRIPTION OF THE DRAWINGS

The invention is illustrated by way of examples which are not a limitation, and the figures of the accompanying drawings in which references denote corresponding parts, and in which.

DETAILED DESCRIPTION OF THE INVENTION

As illustrated in the attached Figures, the method of the present invention is designed to assist in identifying a fixed point of reference on a human jaw by using a mandibular c-clamp.

Figure 1:
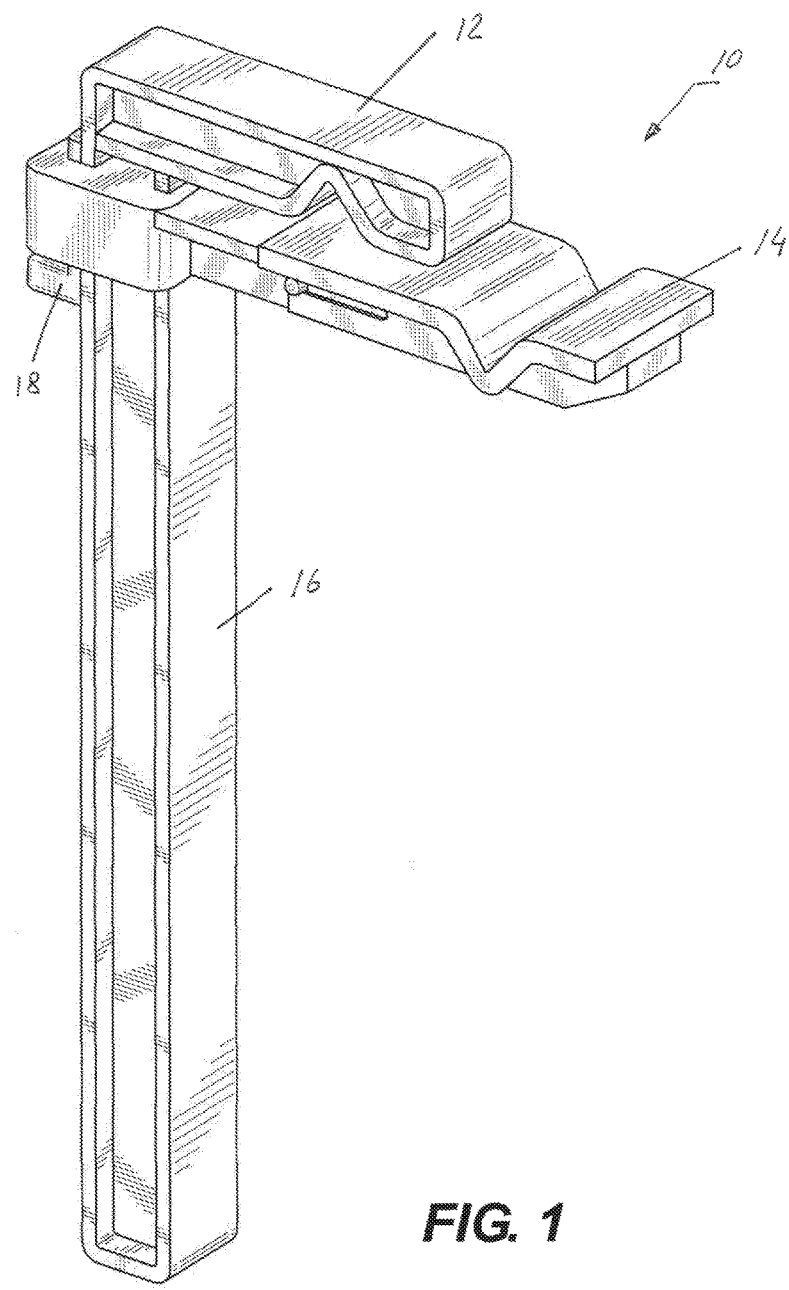
FIG. 1 is a perspective view of the mandibular c-clamp utilized by the method of the present invention.
Figure 2:
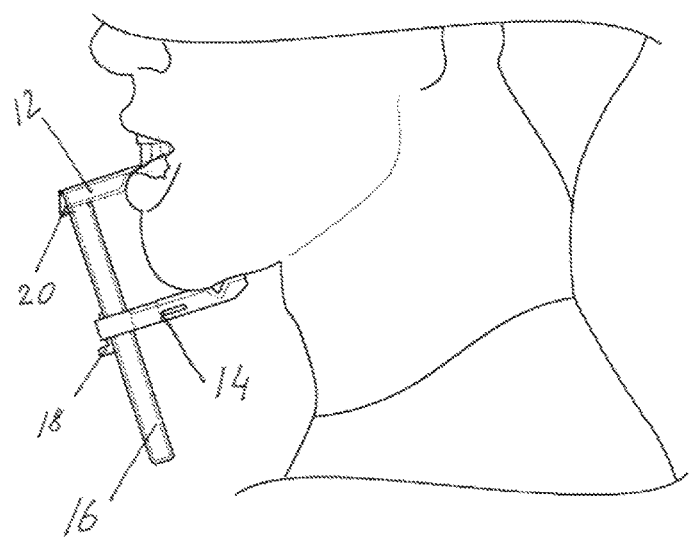
FIG. 2 is a side view of the mandibular c-clamp secured to the mandible of a patient.
Figure 4:
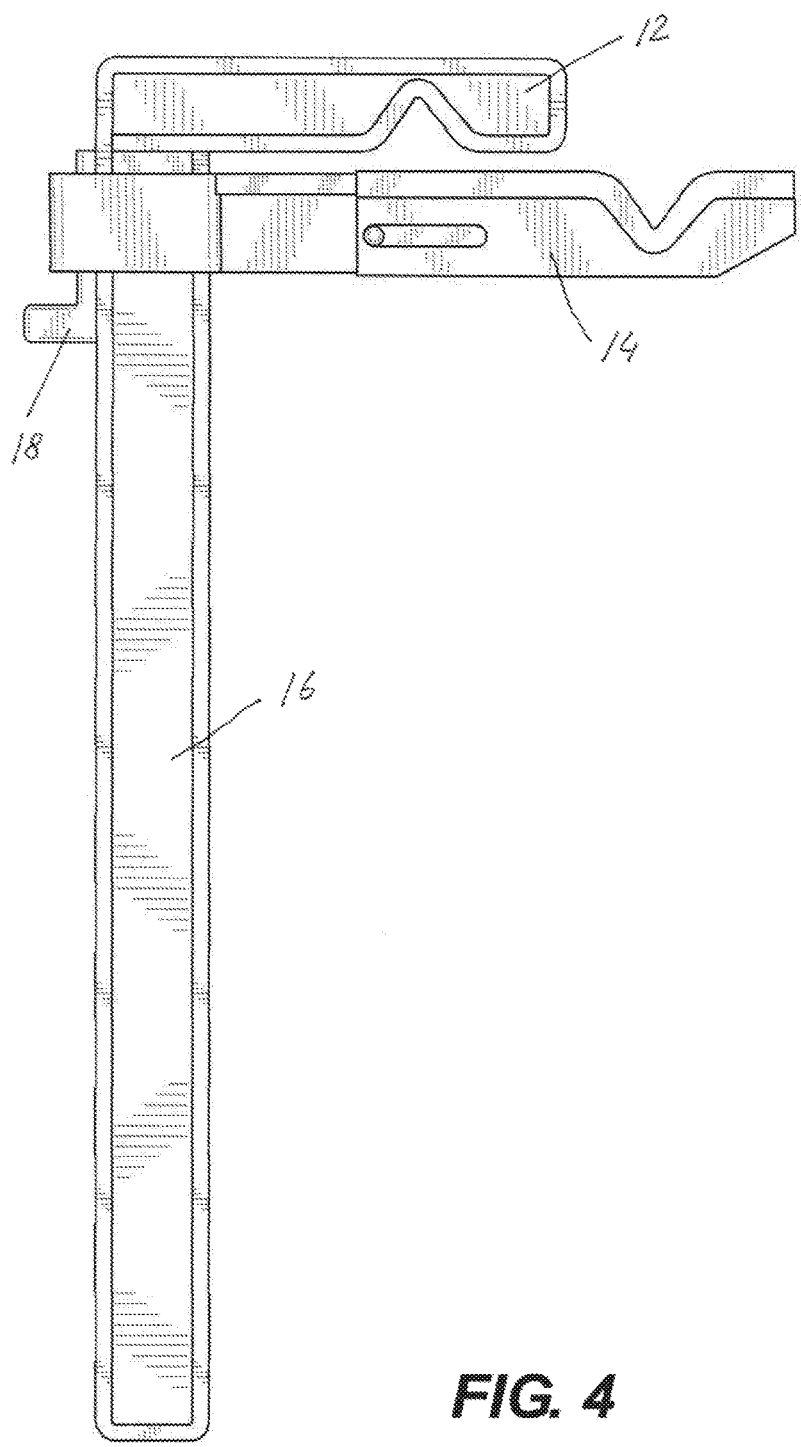
FIG. 4 is a side view of the mandibular c-clamp utilized by the method of the present invention.

As shown in FIGS. 1 and 4, in the preferred embodiment, the mandibular c-clamp 10 is a relatively small adjustable mandibular clamp preferably made of either single use plastic material, or autoclavable stainless steel. C-clamp 10 preferably includes an upper prong 12, a lower prong 14, a shaft 16 and a wedge 18. The upper prong 12 is an intraoral component and is preferably fixedly secured to the top of the shaft 16 and includes a recess. The lower prong 14 and the shaft 16 are the extraoral components, where the lower prong 14 is preferably movable along the shaft 16 in the vertical direction to accommodate various heights of human mandibles. As shown in FIGS. 1-2 and 4, the lower prong 14 has a two-part construction, the first part of the lower prong being securable to the shaft and only being movable vertically with respect to the shaft, and the second part of the lower prong being adjustably secured to the first part and being movable horizontally with respect to the shaft and the first part of the lower prong. Lower prong's position on the shaft can be selectively secured using the wedge 18. Further, the lower prong 14 is preferably adjustable in length to accommodate various depths of human mandibles.

The method of the present invention compensates for the movement of the cervicocranium during mandibular movement to generate the most precise diagnostic analysis. The method utilizes finding and registration fixed reference and control points from which the system can take the measurements utilizing sensors: (1) trago-orbital plane created by the trago-orbital lines (as reference point), more particularly described in U.S. Pat. No. 9,579,046, the disclosure of which is incorporated herein by reference; and (2) Sensor Point on the mandible (as a measurement point to trace mandibular movements).

Figure 3:
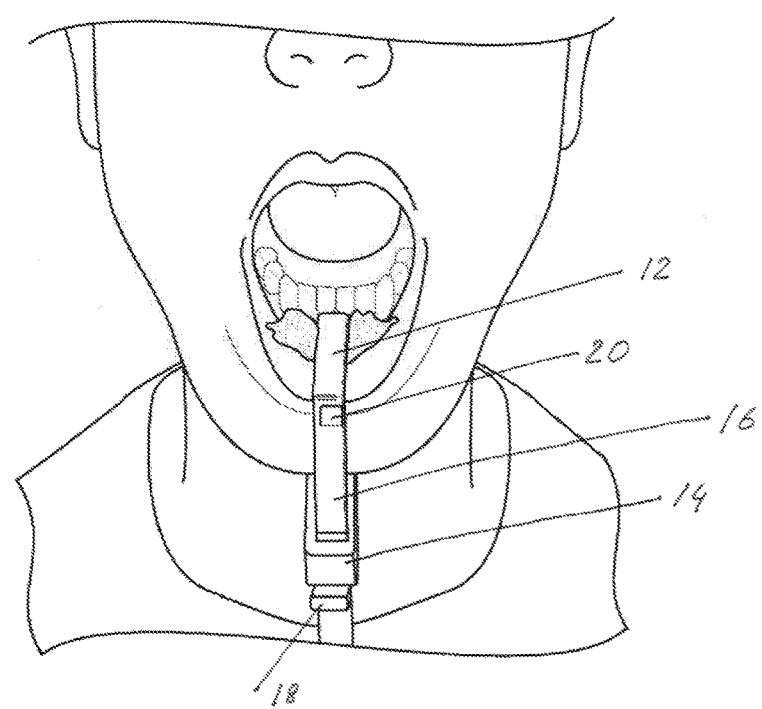
FIG. 3 is a front view of the mandibular c-clamp secured to the mandible of a patient.

In use, a lidocaine gel is first applied to the area of the central lower frenulum to numb the area. Once the gel is applied, the area is covered with sterile gauze. As shown in FIGS. 2 and 3, the upper prong 12 is then inserted into the patient's mouth and positioned onto the gauze such that the recess of the upper prong at least partially accommodates the gauze and the patient's soft tissues. The lower prong 14 is then moved along the shaft 16 to close on the chin gently compressing the soft tissue. Prior to closing on the patient's chin, the lower prong can be adjusted (i.e., expanded or contracted) to accommodate the patient's chin by moving the second part of the lower prong horizontally with respect to the first part and the shaft. Finally, the wedge is applied at that point to secure the attachment.

The clamp is preferably positioned in the center of the mandible next to the central lower frenulum on top side and in the area of Spina Mentalis just below the Mandibular Symphysis. Anesthesia by lidocaine spray can be locally applied, but very seldom necessary for the clamp positioning.

It is empirically studied and concluded that any soft tissue intraoral attachment to the mandible extending from the central frenulum and extending to the area on the chin are biomechanically unaffected by various mandibular movements, and that the various mandibular movements do not affect the secure attachment positioning in that location provided that the clamp stays compressed. Wedge 18 provides this necessary compression.

A 3-axial sensor 20 can then be secured to a specifically designated area on the C-clamp. Sensor 20 is preferably a 3D axiometer. Therefore, after calibration procedures, diagnostic tracings of the mandibular movements can be taken without any errors and in true 3D. As a result, the method of the present invention precisely and reliably identifies a fixed point of reference on a human jaw. The method can be used repeatedly without jeopardizing the precision. Moreover, the method can be used regardless of whether the patient has teeth.

In the preceding specification, the invention has been described with reference to specific exemplary embodiments thereof. It will however, be evident that various modifications and changes may be made thereto without departing from the broader spirit and scope of the invention as set forth in the claims that follow. The specification and drawings are accordingly to be regarded in an illustrative manner rather than a restrictive sense.

We claim as follows:

1. A method for identifying a fixed point of reference on a human jaw, the method comprising the steps of:
    providing a mandibular c-clamp, the mandibular c-clamp having a shaft, an upper prong fixedly connected to said shaft and further comprising a recess, a lower prong movable along said shaft, said lower prong having a two-part construction, a first part of the lower prong being securable to said shaft and only being movable vertically with respect to said shaft and a second part of the lower prong being adjustably secured to said first part and being movable horizontally with respect to said shaft and said first part of said lower prong, and a wedge configured to selectively secure said first part of the lower prong to said shaft;
    positioning a sterile material over a central lower frenulum of a patient;
    inserting said upper prong of said mandibular c-clamp into a patient's mouth and positioning said upper prong over the central lower frenulum of the patient such that said recess at least partially accommodates said sterile material and said patient's soft tissues;
    positioning said second part of the lower prong under a patient's chin and adjusting said lower prong of said mandibular c-clamp to accommodate a depth of a patient's jaw by moving said second part of the lower prong horizontally with respect to the first part and the shaft;
    once the correct horizontal position of said second part of the lower prong is identified, moving said lower prong of said mandibular c-clamp along said shaft to close on a patient's chin compressing said patient's soft tissue between said upper prong and said second part of the lower prong;
    securing a position of said lower prong using said wedge so that said lower prong is no longer movable along said shaft; and
    securing a sensor to a designated area of said mandibular c-clamp so as to provide a reference point.

2. The method according to claim 1, wherein said lower prong is positioned in an area of Spina Mentalis just below a Mandibular Symphysis of the patient.

3. The method according to claim 1, further comprising a step of applying local anesthesia prior to inserting said upper prong.

* * * * *